US007510715B2

(12) United States Patent
Aliberti et al.

(10) Patent No.: US 7,510,715 B2
(45) Date of Patent: Mar. 31, 2009

(54) PROTOZOAN DERIVED COMPOSITIONS AND METHODS OF USE THEREOF

(75) Inventors: Julio Aliberti, Durham, NC (US); John Andersen, Kensington, MD (US); Hana Golding, Rockville, MD (US); Alan Sher, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 113 days.

(21) Appl. No.: 11/177,934

(22) Filed: Jul. 8, 2005

(65) Prior Publication Data

US 2006/0148696 A1 Jul. 6, 2006

Related U.S. Application Data

(60) Provisional application No. 60/586,884, filed on Jul. 8, 2004.

(51) Int. Cl.
*A61K 39/00* (2006.01)
*A61K 39/012* (2006.01)
*A61K 39/21* (2006.01)

(52) U.S. Cl. ............... 424/188.1; 424/134.1; 424/139.1; 424/185.1; 424/265.1; 424/273.1

(58) Field of Classification Search ................. None
See application file for complete search history.

(56) References Cited

OTHER PUBLICATIONS

Golding et al., Inhibition of HIV-1 infection by a CCR5-binding cyclophilin from *Toxoplasma gondii*, Blood, Nov. 1, 2003, vol. 102, No. 9, pp. 3280-3286.*

High et al., Isolation, cDNA Sequences, and Biochemical Characterization of the Major Cyclosporin-binding Proteins of *Toxoplasma gondii*, The Journal of Biological Chemistry, Mar. 1994, vol. 269, No. 12, pp. 9105-9112.*
Towers et al., Cyclophilin A modulates the sensitivity of HIV-1 to host restriction factors, Nature Medicine, Aug.-Sep. 2003, vol. 9, No. 9, pp. 1138-1143.*
Bosco et al. PNAS, Apr. 2002, vol. 99, No. 8, pp. 5247-5252.*
Legrand et al. HIV Clinical Trials, 2003, vol. 4, No. 3, pp. 170-183.*
Braaten et al., "Cyclophilin A regulates HIV-1 infectivity, as demonstrated by gene targeting in human T cells", The EMBO Journal, 20(6):1300-1309 (2001).
Sherry et al., "Role of cyclophilin A in the uptake of HIV-1 by macrophages and T lymphocytes", Proc. Natl. Acad. Sci., 95L1758-1763 (1998).
Golding et al., "Inhibition of HIV-1 infection by a CCR%-binding cyclophilin from *Toxoplasma gondii*" Blood, 102(9):3280-3286 (2003).
Lawn et al., "Contribution of Immune Activation to the Pathogenesis and Transmission of Human Immunodeficiency Virus Type 1 Infection", Clinical Microbiology Reviews, 14(4)753-777 (2001).
Doytchinova et al., "Proteomics in Vaccinology and Immunobiology: An Informatics Perspective of the Immunone", Journal of Biomedicine and Biotechnology, 203:5 pp. 267-290 (2003).
NCBI Sequence Accession No. AAA17998, May 1994.

* cited by examiner

*Primary Examiner*—Bruce Campell
*Assistant Examiner*—Sharon Hurt
(74) *Attorney, Agent, or Firm*—Edwards Angel Palmer & Dodge LLP; Peter F. Corless; Jonathan M. Sparks

(57) ABSTRACT

The instant invention relates to methods for treating a subject suffering from or susceptible to an autoimmune disease or disorder, or a disease or disorder having an autoimmune component, comprising administering to the subject an effective amount of cyclophilin or a biologically active fragment thereof.

11 Claims, 4 Drawing Sheets

FIGURE 4A (SEQ ID NO:1)

```
1   AATTCCAAAA TGAAGCTCGT GCTGTTTTTC CTCGCTCTTG CGGTGTCTGG CGCCGTGGCA
61  GAAAATGCCG GAGTCAGAAA GGCGTACATG GATATCGACA TCGACGGAGA ACATGCCGGG
121 CGCATTATCT TGGAGCTCCG TGAGGACATC GCTCCCAAAA CTGTCAAGAA CTTCATTGGC
181 CTTTTCGACA AGTACAAGGG CAGCGTTTTC CACCGTATCA TCCCCGACTT CATGATCCAG
241 GGAGGAGATT TCGAGAACCA CAACGGCACT GGAGGACACA GCATCTACGG CCGAAGATTT
301 GACGACGAAA ACTTTGATTT GAAGCACGAG CGAGGCGTCA TCTCTATGGC GAACGCCGGT
361 CCGAACACCA ATGGCAGCCA ATTTTTCATC ACCACCGTGA AGACAGAGTG GCTCGACGCC
421 AGACACGTTG TTTTCGGGAA GATCACAACT GAGTCGTGGC CTACCGTCCA GGCTATTGAG
481 GCTCTCGGCG GCAGCGGCGG CCGCCGTCT AAGGTCGCGA AAATCACGGA CATTGGTTTG
541 TTGGAGTAAA TCGAGAAGAT CCTGTGTACA TCTGGATGCA CGTGTCGTTT CCCCTGATAT
601 CTATTCGTGT GAGCAAGTGT GCCCTCTTCC CGACGAAAGT GGGGAGTCCA CACCACTGAA
661 CGTTTTTTTA AACATTTCTA AATACTAGAC TCTGTCG
```

FIGURE 4B (SEQ ID NO:2)

```
1   MKLVLFFLAL AVSGAVAENA GVRKAYMDID IDGEHAGRII LELREDIAPK TVKNFIGLFD
61  KYKGSVFHRI IPDFMIQGGD FENHNGTGGH SIYGRRFDDE NFDLKHERGV ISMANAGPNT
121 NGSQFFITTV KTEWLDARHV VFGKITTESW PTVQAIEALG GSGGRPSKVA KITDIGLLE
```

PROTOZOAN DERIVED COMPOSITIONS AND METHODS OF USE THEREOF

RELATED APPLICATIONS

This application claims the benefit of U.S. Provisional Application No.: 60/586,884, filed on Jul. 8, 2004, the entire contents of which are expressly incorporated herein by reference.

GOVERNMENT SUPPORT

Research supporting this application was carried out by the United States of America as represented by the Secretary, Department of Health and Human Services.

BACKGROUND OF THE INVENTION

The chemokine receptors CCR5 and CXCR4 are the predominant coreceptors for HIV-1 in vivo, and all HIV-1 strains are currently classified as R5, X4, or R5x4.[1] As members of the 7 transmembrane-domain G protein-coupled receptor (GPCR) superfamily, CCR5 and CXCR4 share common structural features, including an extracellular N-terminus, 3 extracellular domains, 3 intracellular domains, and an intracytoplasmic C-terminal tail. The functions of CCR5 and CXCR4 as chemokine receptors and HIV-1 coreceptors are separable, in that the binding sites for their biologic ligands (ie, chemokines) and for HIV-1 gp120 were found to be discrete with some overlap.[2-5] Thus, binding of a given protein or small molecule to the HIV-1 coreceptor is not necessarily predictive of HIV-1 inhibition.

Previously, it was reported that a soluble tachyzoite extract of the protozoa *Toxoplasma gondii* (STAg) uses the chemokine receptor CCR5 on murine dendritic cells to induce interleukins-12 (IL-12) production.[6] The active component in STAg that signals through CCR5 was recently identified as cyclophilin-18(C-18).[7]

HIV infection and AIDS provide a growing medical problem for health care professionals around the world. New and effective treatments are needed to slow the spread, and eventually eradicate, the disease.

BRIEF SUMMARY OF THE INVENTION

In one aspect, the instant invention provides a method for treating a subject suffering from or susceptible to an autoimmune disease or disorder, or a disease or disorder having an autoimmune component comprises administering to the subject an effective amount of cyclophilin or an active portion thereof.

In one embodiment, the subject is suffering from or susceptible to an HIV infection. In a related embodiment, the HIV is a CCR5 specific HIV. In another related embodiment, the subject is a human.

In related embodiments, a biologically active fragment of cyclophilin that is encoded by a nucleic acid molecule that is at least 85% or 95% identical to SEQ ID NO:1, or a fragment thereof, is used in the method. In another related embodiment, the cyclophilin used in the method is at least 85% or 95% identical to SEQ ID NO:2.

In one embodiment, the cyclophilin is a protozoan cyclophilin, e.g., from the genus *Toxoplasma*. In a specific embodiment, the cyclophilin is from the species *gondii*. In specific embodiments, the ID50 is 10 µg/ml or less, 5 µg/ml or less, or 2.5 µg/ml or less. In another aspect, the instant invention provides a method of treating or preventing HIV infection in a subject comprising administering to the subject an effective amount of a cyclophilin, or biologically active fragment thereof, wherein the cyclophilin is capable of inhibiting HIV infection in a cell, thereby treating or preventing HIV infection in a subject.

In one embodiment, the subject is suffering from or susceptible to an HIV infection. In a related embodiment, the HIV is a CCR5 specific HIV. In another related embodiment, the subject is a human.

In related embodiments, a biologically active fragment of cyclophilin that is encoded by a nucleic acid molecule that is at least 85% or 95% identical to SEQ ID NO:1, or a fragment thereof, is used in the method. In another related embodiment, the cyclophilin used in the method is at least 85% or 95% identical to SEQ ID NO:2.

In one embodiment, the cyclophilin is a protozoan cyclophilin, e.g., from the genus *Toxoplasma*. In a specific embodiment, the cyclophilin is from the species *gondii*.

In specific embodiments, the $ID_{50}$ is 10 µg/ml or less, 5 µg/ml or less, or 2.5 µg/ml or less.

In another aspect, the invention provides a method of inhibiting HIV infection of macrophages or T-cells comprising, contacting said macrophage or T-cell with an effective amount of a cyclophilin, cyclophilin, or biologically active fragment thereof, wherein the cyclophilin is capable of inhibiting HIV infection or a cell, thereby inhibiting the infection of macrophages or T-cells by HIV.

In one embodiment, the subject is suffering from or susceptible to an HIV infection. In a related embodiment, the HIV is a CCR5 specific HIV. In another related embodiment, the subject is a human.

In related embodiments, a biologically active fragment of cyclophilin that is encoded by a nucleic acid molecule that is at least 85% or 95% identical to SEQ ID NO:1, or a fragment thereof, is used in the method. In another related embodiment, the cyclophilin used in the method is at least 85% or 95% identical to SEQ ID NO:2.

In one embodiment, the cyclophilin is a protozoan cyclophilin, e.g., from the genus *Toxoplasma*. In a specific embodiment, the cyclophilin is from the species *gondii*.

In specific embodiments, the $ID_{50}$ is 10 µg/ml or less, 5 µg/ml or less, or 2.5 µg/ml or less.

In another aspect, the invention provides a pharmaceutical composition comprising cyclophilin, or a biologically active fragment thereof, and a pharmaceutically acceptable carrier.

In a related embodiment, the pharmaceutical composition is for the treatment or prevention of an HIV infection. In a related embodiment, the pharmaceutical composition further comprises one or more additional antiviral compounds, e.g., anti-HIV compounds.

In a related embodiment, the pharmaceutical composition comprises cyclophilin, or biologically active fragment thereof, that is encoded by a nucleic acid molecule that is at least 85% or 95% identical to SEQ ID NO:1, or a fragment thereof, or a protein, or biologically active fragment thereof that is at least 85% or 95% identical to SEQ ID NO:2, or a fragment thereof.

In a related embodiment, the pharmaceutical composition comprises a cyclophilin that is a protozoan cyclophilin, e.g., from the genus *Toxoplasma*. In a specific embodiment, the cyclophilin is from the species *gondii*.

In another embodiment, the invention provides a kit comprising a pharmaceutical composition described herein and instructions for use.

BRIEF DESCRIPTION OF THE DRAWINGS

FIG. 4A-B depicts the nucleic acid and polypeptide sequence of *T. gondii* cyclophilin C-18. FIG. 4A depicts the nucleic acid sequence of *T. gondii* cyclophilin C-18 (SEQ ID NO:1). FIG. 4B depicts the polypeptide sequence of *T. gondii* cyclophilin C-18 (SEQ ID NO:2).

DETAILED DESCRIPTION OF THE INVENTION

Figure 1:
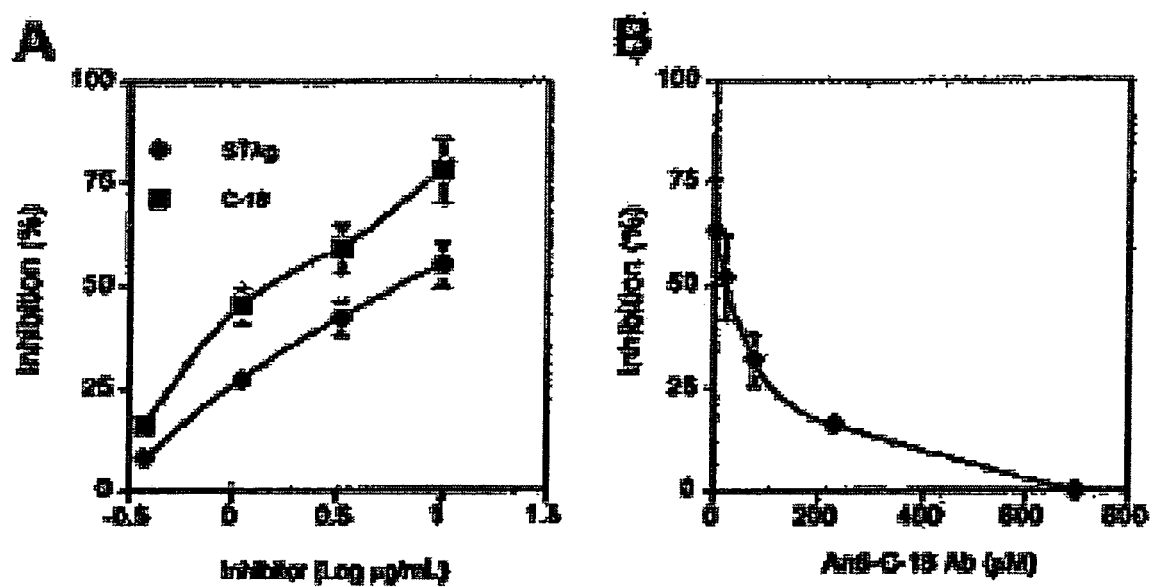
FIGS. 1A-B demonstrate that cyclophilin is the principal fusion-inhibiting component in STAg and is responsible for inhibition of HIV-1. (A) Inhibition of HV-1 envelope-mediated cell fusion with STAg and Cyclophilin (C-18) from *T gondii*. PM1 cells were incubated with serial dilutions of STAg and C-18 for one hour at 37° C. and then mixed (1:1, in triplicates) with 12E1 cells infected overnight with recombinant vaccinia (vCB28) expressing JR-FL envelope. Syncytia were scored between 3 and 4 hours of incubation. Calculated $ID_{50}$ values were as follows: STAg, 7 ug/mL; C-18, 2 ug/mL. Data represent 4 different experiments. No inhibition was observed with recombinant human cyclophilin or with *P falciparum* cyclophilin (data not shown). (B) Antibodies to C-18 inhibit STAg-mediated Inhibition of HIV-1 fusion. PM1 cells were incubated with STAg (10 ug/mL) In the presence of Increasing concentrations of an immunoglobulin G (IgG) fraction from rabbit antiserum raised against recombinant C-18 (1499). 12E1 cells expressing R5 envelope (JR-FL) were added after one hour at 37° C., and syncytia were scored after 3 to 4 hours. Control cultures (no inhibitor added) contained between 400 to 500 syncytia per well. IgG from a control antiserum prepared against an irrelevant peptide (1492) did not block STAg-mediated inhibition of HIV-1 fusion (not shown). The data are representative of 3 experiments performed. Error bars represent SD of the means of 3 replicates per data point.

Disclosed herein are methods and treatments using *T. gondii* cyclophilin, or a biologically active fragment thereof, as anti-viral compounds. Further disclosed herein is a method of treating HIV-1 infections and autoimmune related disorders with *T. gondii* cyclophilin, or a biologically active fragment thereof.

The activation of murine den drift cells by *Toxoplasma gondii* has recently been shown to depend on a parasite protein that signals through the chemokine receptor CCR5. The instant invention is based, at least in part, on the discovery that cyclophilin-18 (C-18), is an inhibitor of HIV-1 cell fusion and infection. *T gondli* C-18 efficiently blocked syncytium formation between human T cells and effector cells expressing R5 but not X4 envelopes. C-18 also protected peripheral blood leukocytes from infection with multiple HIV-1 R5 primary isolates from several clades. C-18 bound directly to human CCR5, and this inter-action was partially competed by the B-chemokine macrophage inflammatory protein 1B (MIP-10) and by HIV-1 R5 gp120. In contrast to several other antagonists of HIV coreceptor function, C-18 mediated inhibition did not induce B-chemokines or cause CCR5 down-modulation, suggesting direct blocking of envelope binding to the receptor.

The instant invention is also based, at least in part, on the discovery that binding of *T gondii* cyclophilin-18 to human cells expressing CCR5 blocks HIV-1 envelope-mediated fusion and protects peripheral blood lymphocytes (PBLs) from infection with multiple R5 primary HIV-1 isolates. The results described in the Experiments support the use of C-18 as an inhibitor of HIV-1 transmission.

Nucleic Acid Molecules

The methods of the instant invention use isolated or purified, nucleic acid molecules that encode a cyclophilin polypeptide described herein, e.g., a full length cyclophilin protein or a fragment thereof, e.g., a biologically active fragment of a cyclophilin protein. Also included is a nucleic acid fragment suitable for use as a hybridization probe, which can be used, e.g., to identify a nucleic acid molecule encoding a polypeptide used in the methods of the invention, cyclophilin mRNA, and fragments suitable for use as primers, e.g., PCR primers for the amplification or mutation of nucleic acid molecules.

In one embodiment, the methods of the invention use nucleic acid molecule of SEQ ID NO:1, or a portion of any of this nucleotide sequence. In one embodiment, the nucleic acid molecule includes sequences encoding the *Toxoplasma gondii* cyclophilin protein (i.e., SEQ ID NO:1). In another embodiment, the nucleic acid molecule encodes a sequence corresponding to a fragment of the protein of SEQ ID NO:2.

In one embodiment, the nucleic acid molecule used in the methods of the present invention includes a nucleotide sequence which is at least about: 60%, 65%, 70%, 75%, 80%, 85%, 90%, 91%, 92%, 93%, 94%, 95%, 96%, 97%, 98%, 99%, or more identical to the entire length of the nucleotide sequence shown in SEQ ID NO:1, or a portion, preferably of the same length, of any of these nucleotide sequences. Calculations of homology, or sequence identity (the terms "homology" and "identity" are used interchangeably herein) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) J. Mol. Biol. 48:444-453 algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to cyclophilin nucleic acid molecules of the invention. BLAST protein searches can be performed with the XBLAST program, score=50, wordlength=3 to obtain amino acid sequences homologous to cyclophilin protein molecules of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See www.nebi.nlm.nih.gov.

Cyclophilin Nucleic Acid Fragments

Nucleic acid molecules used in the methods of the invention can include only a portion of the nucleic acid sequence of SEQ ID NO:1. For example, such a nucleic acid molecule can include a fragment which can be used as a probe or primer or a fragment encoding a portion of a cyclophilin protein, e.g., an immunogenic or biologically active portion of a cyclophilin protein. A fragment can comprise those nucleotides of SEQ ID NO:1, which encode a biologically active fragment of cyclophilin. The nucleotide sequence of the cyclophilin gene allows for the generation of probes and primers designed for use in identifying and/or cloning other cyclophilin family members, or fragments thereof, as well as cyclophilin homologs, or fragments thereof, from other species.

A nucleic acid fragment can include a sequence corresponding to a domain, region, or functional site described herein. A nucleic acid fragment can also include one or more domains, regions, or functional sites described herein.

A nucleic acid fragment encoding a "biologically active portion of a cyclophilin polypeptide" can be prepared by isolating a portion of the nucleotide sequence of SEQ ID NO:1, which encodes a polypeptide having a cyclophilin biological activity (e.g., the biological activities of the cyclophilin proteins are described herein), expressing the encoded portion of the cyclophilin protein (e.g., by recombinant expression in vitro) and assessing the activity of the encoded portion of the cyclophilin protein.

A nucleic acid fragment encoding a biologically active portion of a cyclophilin polypeptide, can comprise a nucleotide sequence which is greater than 50 or more nucleotides in length.

In preferred embodiments, a nucleic acid includes a nucleotide sequence which is about 50, 100, 150, 200, 250, 300, 450, 500 or more nucleotides in length and hybridizes under stringent hybridization conditions to a nucleic acid molecule of SEQ ID NO:1.

Cyclophilin Nucleic Acid Variants

The invention further makes use of nucleic acid molecules that differ from the nucleotide sequence shown in SEQ ID NO:1. Such differences can be due to degeneracy of the genetic code (and result in a nucleic acid which encodes the same cyclophilin proteins as those encoded by the nucleotide sequence disclosed herein). In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology.

Nucleic acids can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:1 or a fragment of this sequence. Such nucleic acid molecules can readily be identified as being able to hybridize under stringent conditions, to the nucleotide sequence shown in SEQ ID NO:1 or a fragment of the sequence.

Nucleic acid molecules encoding other cyclophilin family members and, thus, which have a nucleotide sequence which differs from the cyclophilin sequences of SEQ ID NO:1 but retain on a functional activity of the protein encoded by SEQ ID NO:1 are intended to be within the scope of the invention.

Isolated Cyclophilin Polypeptides

In another aspect, the invention features methods using an isolated cyclophilin protein, or fragment, e.g., a biologically active fragment. Cyclophilin can be isolated using standard protein purification techniques. Cyclophilin or fragments thereof can be produced by recombinant DNA techniques or synthesized chemically.

In a one embodiment, the cyclophilin polypeptide has an overall sequence similarity of at least 60%, preferably at least 70%, more preferably at least 80, 90, or 95%, with a polypeptide of SEQ ID NO:2, or a fragment thereof.

In another embodiment the cyclophilin protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2.

In one embodiment, a biologically active portion of a cyclophilin protein includes a fragment that is capable of inhibiting HIV envelope-mediated fusion. Moreover, other biologically active portions, in which other regions of the protein are deleted, can be prepared by recombinant techniques and evaluated for one or more of the functional activities of a native cyclophilin protein.

In a preferred embodiment, the cyclophilin protein has an amino acid sequence shown in SEQ ID NO:2. In other embodiments, the cyclophilin protein is sufficiently or substantially identical to SEQ ID NO:2. In yet another embodiment, the cyclophilin protein is sufficiently or substantially identical to SEQ ID NO:2 and retains the functional activity of the protein of SEQ ID NO:2.

In another aspect, the invention also features a variant of a cyclophilin polypeptide. Variants of the cyclophilin proteins can be generated by mutagenesis, e.g., discrete point mutation, the insertion or deletion of sequences or the truncation of a cyclophilin protein. Preferably, treatment of a subject with a variant having a subset of the biological activities of the naturally occurring form of the protein has fewer side effects in a subject relative to treatment with the naturally occurring form of the cyclophilin protein.

Variants of a cyclophilin protein can be identified by screening combinatorial libraries of mutants, e.g., truncation mutants, of a cyclophilin protein for activity.

Libraries of fragments e.g., N terminal, C terminal, or internal fragments, of a cyclophilin protein coding sequence can be used to generate a variegated population of fragments for screening and subsequent selection of variants of a cyclophilin protein.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify cyclophilin variants (Arkin and Yourvan (1992) Proc. Natl. Acad. Sci. USA 89:7811-7815; Delgrave et al. (1993) Protein Engineering 6:327-331).

Methods of making the proteins used in the methods of the instant invention are well known to one of skill in the art and can be performed using only routine experimentation.

Recombinant Expression Vectors, Host Cells and Genetically Engineered Cells

Vectors, preferably expression vectors, containing a nucleic acid encoding a polypeptide described herein are useful in the practice of the methods of the instant invention. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a cyclophilin nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., cyclophilin proteins, mutant forms of cyclophilin proteins, biologically active fragments of cyclophilin and the like).

The recombinant expression vectors of the invention can be designed for expression of cyclophilin proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

To maximize recombinant protein expression in E. coli is to express the protein in a host bacteria with an impaired capacity to proteolytically cleave the recombinant protein (Gottesman, S., (1990) Gene Expression Technology: Methods in Enzymology 185, Academic Press, San Diego, Calif. 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

The cyclophilin expression vector can be a yeast expression vector, a vector for expression in insect cells, e.g., a baculovirus expression vector or a vector suitable for expression in mammalian cells.

In another embodiment, the recombinant mammalian expression vector is capable of directing expression of the nucleic acid preferentially in a particular cell type (e.g., tissue-specific, or cell specific, regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Baneriji et al. (1983) Cell 33:729-740; Queen and Baltimore (1983) Cell 33:741-748), neuron-specific promoters (e.g., the neurofilament promoter; Byrne and Ruddle (1989) Proc. Nat. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., (1986) Reviews—Trends in Genetics 1:1.

Host cells which include a nucleic acid molecule described herein are also useful in the practice of the instant invention, e.g., a cyclophilin nucleic acid molecule within a recombinant expression vector or a cyclophilin nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein. A host cell can be any prokaryotic or eukaryotic cell.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

Pharmaceutical Compositions and Kits

One or more cyclophilins may be administered as a "cocktail" formulation with other therapeutics, i.e. coordinated administration of one or more compounds of the invention together with one or more other active therapeutics, such as one or more other agents used to treat immune disorders, and/or one or more agents used to treat HIV infections. For instance, a cyclophilin may be administered in coordination with beta interferon or other immune therapy agent, or agents used for treatment of retroviral infections such as a protease inhibitor (e.g. saquinavir, ritonavir, indinavir or AG1343 (Viracept)), AZT, ddI, ddC, d4T, 3TC, FTC, DAPD, acyclovir, and the like.

The nucleic acid and polypeptides, biologically active fragments thereof (also referred to herein as "active compounds") of the invention can be incorporated into pharmaceutical compositions. Such compositions typically include the nucleic acid molecule or protein, and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, kit or dispenser together with instructions, e.g., written instructions, for administration, particularly such instructions for use of the active agent to treat against a disorder or disease as disclosed herein, including an autoimmune disease or disorder, treatment in connection with an organ or tissue transplant, as well as other diseases or disorders with an autoimmune component such as AIDS. The container, pack, kit or dispenser may also contain, for example, cyclophilin polypeptide, or biologically active fragment thereof, a nucleic acid sequence encoding a cyclophilin peptide, or fragment thereof, or a cyclophilin-expressing cell.

Methods of Treatment

The compositions disclosed herein may be useful as antiviral compositions, anti-inflammatory compositions or for the treatment of autoimmune disease, e.g., such as those related to AIDS.

The invention provides therapeutic methods and compositions for the prevention and treatment of autoimmune disease and related conditions such as AIDS and organ/tissue rejection. In particular, the invention provides methods and compositions for the prevention and treatment of autoimmune and related diseases in humans as well as other animals through the administration of cyclophilin.

In one embodiment, the present invention contemplates a method of treatment, comprising: a) providing: i) a mammalian patient particularly human who is either at risk for autoimmune disease or who has symptoms of autoimmune disease, ii) cyclophilin, and; b) administering the cyclophilin to the patient.

The term "symptoms of autoimmune disease" is herein defined as any abnormal symptoms than can be attributed to the generation of autoreactive B and/or T cells. For example, autoantibodies are a common symptom associated with autoimmune disease.

The term "at risk for autoimmune disease" is herein defined as individuals with familial incidence of autoimmunity. For example, many autoimmune diseases are associated with genetic factors such as certain HLA specificities.

The term "autoimmune and related diseases" refers to those disease states and conditions wherein the immune response of the patient is directed against the patient's own constituents, resulting in an undesirable and often terribly debilitating condition. As used herein, "autoimmune disease" is intended to further include autoimmune conditions, syndromes and the like. An "autoantigen" is a patient's self-produced constituent, which is perceived to be foreign or undesirable, thus triggering an autoimmune response in the patient, which may in turn lead to a chain of events, including the synthesis of other autoantigens or autoantibodies. An "autoantibody" is an antibody produced by an autoimmune patient to one or more of his own constituents which are perceived to be antigenic. For example, in AIDS disease the patient eventually produces autoantibodies to CD4 cells, in SLE autoantibodies are produced to DNA, while in many other types of autoimmune diseases autoantibodies are produced to target cells.

The present invention is also not limited by the degree of benefit achieved by the administration of cyclophilin. For example, the present invention is not limited to circumstances where all symptoms are eliminated. In one embodiment, administering a cyclophilin reduces the number or severity of symptoms of an autoimmune disease (e.g., the amount of autoantibody is reduced and/or the amount of pain is reduced). In another embodiment, administering of a cyclophilin may delay the onset of symptoms.

As mentioned above, the indications for which the administration of cyclophilin compositions can be used include in particular autoimmune conditions; HIV infection/AIDS conditions; and conditions associated with or causing transplant rejection, e.g., treatment (including amelioration, reduction, elimination or cure of etiology or symptoms) or prevention (including substantial or complete restriction, prophylaxis or avoidance) of the following:

A) Autoimmune disease and inflammatory conditions, in particular inflammatory conditions with an etiology including an immunological or autoimmune component such as arthritis (for example rheumatoid arthritis, arthritis chronica progrediente and arthritis deformans) and other rheumatic diseases. Specific autoimmune diseases for which the synergistic combination of the invention may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, (autoimmune) inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis. Autoimmune and inflammatory conditions of the skin are also considered to be amenable to treatment and prevention using the synergistic combination of the invention, e.g., psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, and other inflammatory or allergic conditions of the skin, as are inflammatory conditions of the lungs and airways including asthma, allergies, and pneumoconiosis;

B) HIV infection and all related conditions from initial infection to the full complement of AIDS disease and all other AIDS-related disorders (e.g., ARC);

C) Acute organ or tissue transplant rejection, e.g. treatment of recipients of, e.g., heart, lung, combined heart-lung, liver, kidney, pancreatic, skin, bowel, or corneal transplants, especially prevention and/or treatment of T-cell mediated rejection, as well as graft-versus-host disease, such as following bone marrow transplantation; and D) Chronic rejection of a transplanted organ, in particular, prevention of graft vessel disease, e.g., characterized by stenosis of the arteries of the graft as a result of intima thickening due to smooth muscle cell proliferation and associated effects.

Typical subjects for treatment in accordance with the individuals include mammals, such as primates, preferably humans. Cells treated in accordance with the invention also preferably are mammalian, particularly primate, especially human. As discussed above, a subject or cells are suitably identified as in needed of treatment, and the identified cells or subject are then selected for treatment and administered one or more of cyclophilins.

The treatment methods and compositions of the invention also will be useful for treatment of mammals other than humans, including for veterinary applications such as to treat horses and livestock e.g. cattle, sheep, cows, goats, swine and the like, and pets such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

EXAMPLES

It should be appreciated that the invention should not be construed to be limited to the examples that are now described; rather, the invention should be construed to include any and all applications provided herein and all equivalent variations within the skill of the ordinary artisan.

Materials and Methods

Starting Parasite Preparations

*T gondii* tachyzoites (RH88 strain) were cultured in human fibroblasts as previously described[8] under *Mycoplasma*-free conditions. The parasites were then purified by passage over a glass wool column. Soluble tachyzoite antigen (STAg) was prepared from sonicated tachyzoites as described previously[8.]

Reagents and Cell Lines

Recombinant C-18 protein was expressed in *Escherichia coli* and was purified as described previously.[7] Polyclonal anti-C-18 (1492) and control (1499) antibodies were prepared as described previously.[7]

Human cyclophilin and cyclosporin A (CsA) were purchased from Sigma (St. Louis, Mo.). Recombinant *Plasmodium falciparum* cyclophilin (PfCyp19), expressed in *E coli* and purified as previously described,[9] was generously provided by Alan Fairlamb (Welcome Trust Biocentre, Dundee, United Kingdom). Regulated on activation of normal T cells expressed and secreted (RANTES), macrophage inflammatory protein 1α (MIP 1α), and MIP-1β were purchased from Peprotech (Rocky Hill, N.J.). Antibodies against MIP 1α) and MIP-1β were purchased from R&D Systems (Minneapolis, Minn.). CCR5.EGFP and M7-CCR5.EGFP were stably transduced into CEM cells by retroviral vector infection using retroviral vector stocks produced by transfecting 293T cells as previously described.[10] The CEM.NKR-CCR5 cell line was obtained from John Moore (Cornell University Medical School, N.Y.). The PM1 cell line (a $CD4^+CXCR4^+CCR5^+$ derivative of the Hut 78 cell line) was previously described.[11]

CCR5 Binding Assay

Recombinant C-18 was trace labeled with $^{125}I$ by Phoenix Pharmaceuticals (San Carlos, Calif.). CEM (American Type Culture Collection, Manassas, Va.; no. CCL-119, $CXCR4^+$ $CCRR5^-$) and CEM.NKR.CCR5 ($CXCR4^+CCR5^+$)[12] cells were incubated in triplicate with increasing concentrations of $^{125}I$-labeled C-18 or human MIP-1β for 90 minutes at 4° C., and the unbound fraction was sampled following centrifugation. The bound fraction was then measured and the dissociation constant for ligand binding calculated using a Graph Pad Prism software program (Mackiev, Cupertino, Calif.). To assess the specificity of binding, CEM.NKR.CCR5 cells were incubated with 10-μM $^{125}I$-labeled recombinant C-18 in the presence of increasing concentrations of unlabeled C-18, human MIP-1β, human cyclophilin A, PfCyp19, or R5 envelope (Ba-L), or X4 envelope (MN) (from the NIH AIDS Research and Reference Reagents Program, Rockville, Md.) for 90 minutes at 4° C. Cells were then washed and the bound fraction measured radioactively.

Recombinant Vaccinia Viruses and Fusion Inhibition Assay

Recombinant vaccinia viruses vCB28 (JR-FL envelope), vCB28 (Ba-L envelope), and vCB39 (ADA envelope) were kindly provided by Christopher Broder[13] (Uniformed Services University of the Health Sciences, Bethesda, Md.). Syncytium formation was measured at different times after cocculture (1:1 ratio, $1 \times 10^5$ cells each, in triplicate) of target cells (expressing CD4 and coreceptors) and effector cells ($CD4^-$ 12E1 cells[14] infected overnight with 10 pfu/cell of recombinant vaccinia viruses expressing HIV-1 envelopes). For measurement of X4 Env-mediated fusion, we used the human lymphoid cell line TF228.1.16, which stably expresses HIV-1 IIIB/BH10 envelope.[15] Serially diluted inhibitors were added to the target cells for 60 minutes at 37° C. in a humidified $CO_2$ incubator (3 wells per group). Effector cells were added, and synctium formation was followed for 3 to 4 hours. Linear regression curves were generated and used to calculate the 50% inhibitory dose ($ID_{50}$).

HIV-1 Viral Neutralization

HIV-1 LAI (X4 strain) was kindly provided by Keith Peden (CBER, FDA, Bethesda, Md.). The R5 viruses BaL and JR-CSF as well as a panel of primary isolates were obtained from the NIH AIDS Research and Reference Reagent Program (McKesson BioServices, Rockville, Md.). Viral stocks were produced and tittered in phytohemagglutinin (PHA)-activated peripheral blood mononuclear cells (PBMCs). For viral neutralization by STAg or C-18, serially diluted inhibitors (or human cyclophilin control) were added to target cells in 96-well plates ($5 \times 10^4$ cells/well, 5 replicates per group). For infection, we used either PM1 cells or human PBMCs activated with PHA-P (0.25 μg/mL, from Sigma) plus hIL-2 (20 U/mL, from R&D) for 3 days. Cells were plated in 96-well plates and inhibitors were added (5 replicates per dilution). After one hour of incubation at 37° in $CO_2$ incubator, virus was added (100 tissue culture infectious does [$TCID_{50}$]/ well). After 48 hours of incubation at 37° C., unbound virus and inhibitors were washed away, and the plates were cultured for 2 weeks. Supernatants were removed every second day, and the cultures were supplemented with fresh medium. Viral production was determined by measuring p24 in culture supernatants using a commercial enzyme-lined immunosorbent assay kit (NEN Life Sciences Products, Boston, Mass.). p24 production was measured every second day for 2 weeks, and the $ID_{50}$ values were based on results obtained near peak virus production (usually between days 7-11). Viral neutralization is expressed as 50% inhibitory does ($ID_{50}$) calculated according to the method of Reed and Muench as described by Shibata et al.[16]

Receptor Internalization Assay

PMI cells (or CEM.NKR.CCR5 cells) were incubated with either a mixture of RANTES and MIP-1β (1 μg/mL each, from Peprotech) or with C-18 (10 μg/mL) for 2 hours at 37° C. with occasional shaking. The cells were then washed with phosphate-buffered saline buffer containing 0.01% azide and 1% bovine serum albumin (BSA) and were stained with fluorescein isothiocyanate (FITC)-conjugated 2D7 (anti-CCR5; Pharmingen, Sam Diego, Calif.) or FITC-conjugated Leu 3a (anti-hCD4; Becton Dickinson, San Francisco, Calif.), or FITC-isotype control in the cold and were analyzed by flow cytometry using the FL-1 (FITC channel) on a FACScan (Becton Dickinson) with CellQuest software (BD Biosciences, Lincoln Park, N.J.). Delta mean fluorescence channel (Δ MFC) values were calculated by subtracting the mean fluorescent channel (MFC) value of the isotype control from specific antibody staining.

Preparation of Human Macrophages

Elutriated monocytes (MOs) were obtained from the Department of Transfusion Medicine at the National Institutes of Health. For the generation of monocyte-derived macrophages (MDMs), $1.5 \times 10^6$ monocytes were cultured in 6-well plates in Dulbecco modified Eagle medium supplemented with 1000 units/mL granulocyte-macrophage colony-stimulating factor (GM-CSF; immunex, Seattle, Wash.) and 10% pooled heat-inactivated human serum. After 5 to 6 days, floating cells were removed and adherent cells were harvested by scraping them from the surface of the wells with a rubber policeman. MDMs, were 100% $CD3^-$, more than 85% CD14+, and more than 95% $HLA-DR^+$ as previously described.[17,18]

Results

STAg from *T gondii* Inhibits R5 HIV-1 Cell Fusion

We recently demonstrated that STAg is a potent inducer of IL-12 in mouse dendritic cells, and this activity is mediated in part by signaling via the chemokines receptor CCR5.[6,7] It was of interest to determine if STAg also acts via human CCR5 and whether the extract inhibits its function as an HIV-1 coreceptor. Using an HIV-1 envelope-dependent cell-fusion assay, we found that STAg blocked the fusion of R5 envelope-expressing 12E1 cells with PMI target cells ($CD4^+$, $CXCR4^+$, $CCR5^+$). The 50% inhibitory does ($ID_{50}$) ranged between 4.4 and 7.0 μg/mL for cells expressing BaL, ADA, and JR-FL envelopes (Table 1). In contrast, no inhibition of fusion was seen between PMI and the X4 envelope-expressing TF228 target cells (Table 1).

*T gondii* Cyclophilin 18 is Responsible for the STAg-mediated Inhibition of HIV-1 Fusion and Infection of Human Peripheral Blood Mononuclear Cells We have recently shown that the major component in STAg responsible for its CCR5-dependent IL-12-inducing activity in murine dendritic cells (DCs) is an 18-kDa protein identified as cyclophilin 18 (C-18). The C-18 gene was cloned and expressed in *E coli*, and the recombinant protein was purified by reverse phase high-performance liquid chromatography. It was tested in various immunologic assays and used to generate antibodies in rabbits.[7]

Blocking of HIV-1 fusion by C-18 was found to be either similar or superior to that of STAg, even though it constitutes on average only 1.7% of the total protein in the extract[7] (FIG. 1A). To determine if C-18 accounts for all the STAg-associated inhibitory activity, polyclonal anti-C-18 rabbit antibodies in increasing concentration were incubated with STAg (at 10 μg/mL) prior to the fusion assay. As demonstrated in FIG. 1B, anti-C-18 antibodies reversed the STAg-mediated HIV-1 fusion inhibition in a dose-dependent fashion, demonstrating that C-18 is the major protein in the parasite extract with this activity. In contrast with the fusion-inhibitory activity of *T gondii* C-18, neither human-derived nor *Plasmodium falciparum*-derived cyclophilins had any blocking activity on HIV-1 envelope-mediated cell fusion (Table 2).

TABLE 1

STAg Inhibits fusion of cells expressing R5 but not X4 HIV-1 envelope

| Target | Inhibitor (μg/mL) | % Fusion inhibition* R5 | | | X4 |
|---|---|---|---|---|---|
| | | JR/FL | ADA | Ba-L | IIIB |
| PMI† | RANTES (1) | 100 | 99 | 100 | 0 |
| | SDF1 (1) | 0 | 0 | 0 | 99 |
| | STAg (10) | 58 | 69 | 62 | 0 |
| | (3.3) | 31 | 44 | 50 | 0 |
| | (1.0) | 12 | 15 | 23 | 0 |
| | $ID_{50}$ | 7.0 μg/mL | 5.3 μg/mL | 4.4 μg/mL | — |

$ID_{50}$ indicates 50% inhibitory does; —, no inhibitory activity.
*HIV-1 envelope effector cells were generated by infecting 12E1 cells overnight (10 pfu/cell) with the following recombinant vaccinia viruses expressing R5 envelopes; vCB28 (JR-FL), vCB39 (ADA), and vCB43 (Ba-L).
TF228 cell line, expressing IIIB (BH10) Env, was used to measure X-4-envelope fusion. Number of syncytia in control cultures (no inhibitor present) after 4 hours coculture of effector cells with PM1 target cells; JR-FL, 344 ± 28; ADA, 414 ± Ba-L, 400 ± 74; and IIIB, 335 ± 15. All groups were set up in triplicates.
†PM1 T cells express CD4, CXCR4, and CCR5.

*T gondii* Cyclophilins Inhibits Infection of PBMCs with Primary HIV-1 R5 Viruses Further development of C-18 as a coreceptor inhibitor depends on its ability to block infection with cell-free virus. It is important to establish the breadth and efficiency of this activity using multiple primary HIV-1 strains. A panel of either laboratory-adapted or primary clade B and clade C isolates from different global regions were used. As can be seen in Table 3, significant inhibition was observed with all R5 isolates with $ID_{50}$ values ranging between 0.4 and 14 μg/mL. These values are similar to those reported for seven HIV-1 neutralizing mAbs.[19,20] Again, no inhibition of primary X4 isolates was observed, and human cyclophilin did not inhibit HIV-1 infection (Table 3 and data not shown).

Cyclosporin a Inhibits C-18-mediated Blocking of CCR5 Coreceptor Function

Figure 2:
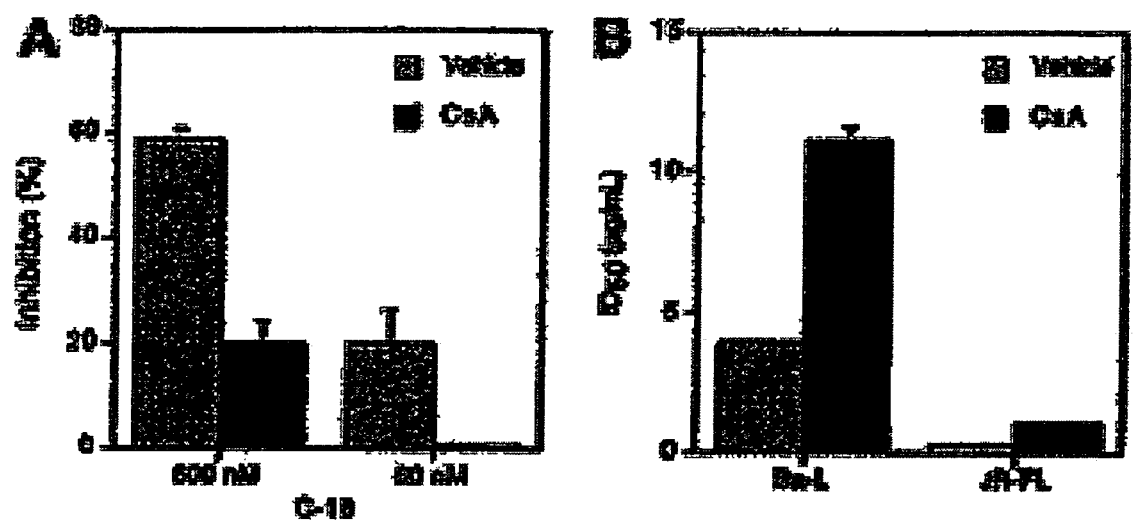
FIGS. 2A-B demonstrate that cyclosporin A, an antagonist of C-18, interferes with the CCR5 fusion-blocking activity. (A) Cyclosporin A (CsA) reduces C-18 blocking of HIV-1 R5-env cell fusion. Serial 3-fold dilutions of C-18 (from 10 to 0.36 ug/mL) were preincubated with CsA (50 ug/mL) for one hour at 37° C. and were then added to PM1 cells for an additional one hour at 37° C. The untreated or treated PM1 cells were mixed with effector cells expressing either JR-FL Env (shown) or Ba-L Env (not shown). Syncytia were scored between 3 and 4 horns. Calculated $ID_{50}$ is as follows: C-18, 4.2 ug/mL; C-18+CsA, 130 ug/mL. The experiment shown is representative of 3 experiments performed. (B) Preincubatlon of C-18 with Cyclosporin A (CsA) significantly reduces its ability to inhibit HIV-1 infection. C-18 (serial dilutions) was incubated with CsA (50 ug/mL) for one hour at 37° C. before adding to PM1 cells for one hour at 37° C. Virus was then added at 100 $TCID_{50}$/well (5 replicates per group) and incubated with cells for 2 days before extensive washings. The $ID_{50}$ values were calculated according to Reed and Muench. Data shown are for day 11 (Ba-L) or day 21 (JR-FL). CsA alone at the same concentration had no inhibitory or stimulatory effects on HIV infection in any of the assays. Error bars represent SD of the means of 3 replicates per data point.

Cyclosporin A (CsA) is a major ligand for cyclophilins and a competitive inhibitor of their peptidyl-prolyl isomerase activity.[21,22] To investigate whether CsA binding to C-18 affects its ability to inhibit HIV-1 fusion, we preincubated serially diluted C-18 with CsA (50 μg/mL) for 60 minutes at 37° C. C-18 alone or the C-18/CsA mixtures were added to PMI target cells for 60 minutes at 37° C., followed by addition of effector cells expressing JR-FL (R5) envelope. Syncytia were scored between 3 and 4 hours. In the presence of CsA, the fusion-inhibiting activity of C-18 was greatly diminished (FIG. 2A). Similarly, CsA preincubation reduced C-18-mediated inhibition of HIV-1 infection in PBMCs, increasing the $ID_{50}$ values for BaL and JR-FL by 3-fold (FIG. 2B).

STAg and C-18-mediated Inhibition of HIV-1 Fusion does not Depend on β-Chemokine Production For some HIV-1 inhibitors, an indirect mechanism was found mediated by induction of β-chemokine production in peripheral blood leukocytes.[23] Several β-chemokines bind to CCR5 and induce its internalization. Thus, it was important to differentiate between direct and indirect mechanisms for the inhibition of HIV-1 fusion mediated by C-18. To address this question, either STAg or C-18 was added to the fusion assay in the presence of antibodies against MIP-1α and MIP-1β. The addition of neutralizing anti-chemokine antibodies had no effect on the fusion-inhibitory activity of either STAg or C-18 (Table 4). The same antibodies could effectively block the inhibitory activity of a mixture of MIP-1α and MIP-1β β-chemokines (Table 4). Identical results were obtained with anti-RANTES antibodies (not shown).

C-18 does not Induce CCR5 Downmodulation

Several classes of inhibitors targeting the HIV coreceptors have been described. In addition to blocking relevant sites, chemokine analogs have been shown to induce rapid downmodulation of chemokine receptors and/or prevent their recycling to the surface.[10,24-26] In contrast, small molecule inhibitors probably exert their effect primarily through receptor occupancy and/or by inducing conformational changes.[27-29] We therefore tested the possibility that C-18 induces downmodulation of CCR5. In 2 cell lines (PMI and CEM.NKR-CCR5), no decreases of either CCR5 or CD4 expression was found after incubation of cells with C-18 at 37° C. for 2 to 3 hours (Table 5) or for 18 hours (data not shown). In the same experiments, a combination of RANTES and MIP-1β did induce downmodulation of CCR5 (Table 5).

To further address this point, we compared fusion inhibition of stably transfected CEM cells expressing either wild-type (WT) CCR5 or M7-CCR5 genes. The M7-CCR5 construct was generated by polymerase chain reaction mutagenesis and contains 7 mutations in the cytoplasmic tail at $Ser^{336}/Ser^{337}/Tyr^{339}/Thr^{340}/Ser^{342}/Thr^{343}/Ser^{349}$, rendering it internalization deficient,[10] C-18 blocked fusion of both WT and M7-CCR5 transfectants, and the $ID_{50}$ values for the M7-CCR5-expressing cells were similar to or lower than those for the WT CCR5-expressing cells (Table 6). Together these data demonstrate that CCR5 internalization is not required for C-18-mediated HIV-1 fusion inhibition.

C-18 Binds Directly to CCR5

Figure 3:
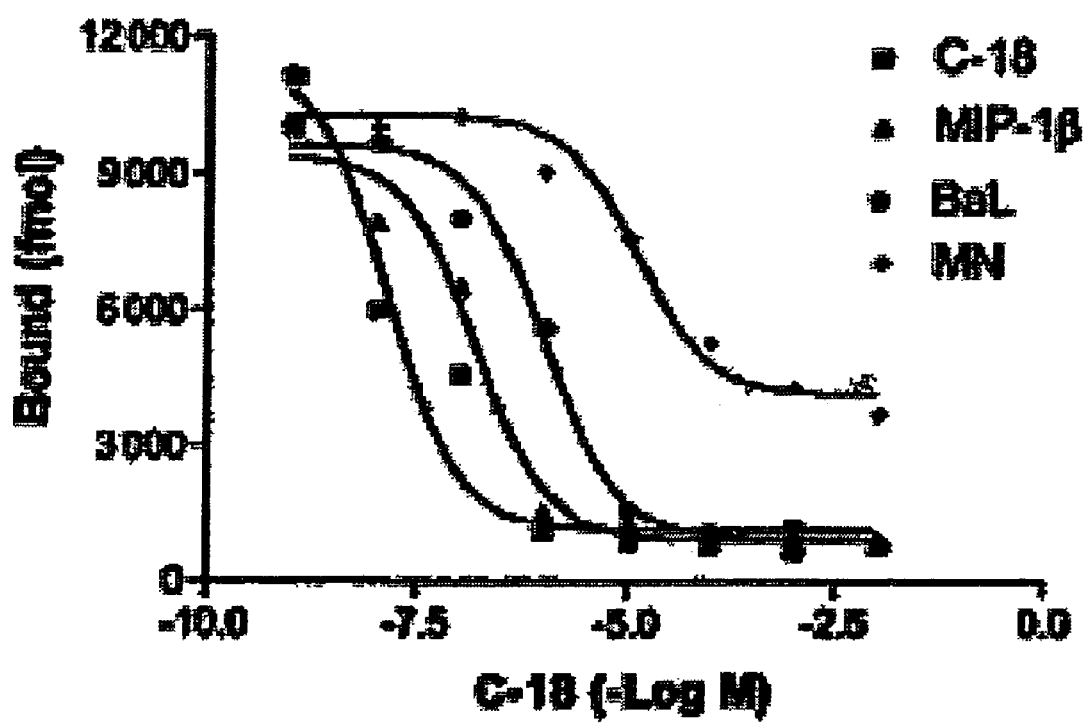
FIG. 3 demonstrates binding of C-18 to CCR5 is partially blocked by MIP-1B and R5 (BaL) envelope. CEM.NKR-CCR5 cells were incubated with increasing concentrations of unlabeled C-18, human MIP-1 B, R5 (Ba-L) Env, or X4 (MN) Erv prior to addition of a fixed concentration of $^{125}$I-C-18. After incubation for 90 minutes at 4° C., the bound counts were measured as described in "Materials and Methods."

Iodinated C-18 was previously shown to bind to a human cell line stably transfected with CCR5 (CEM.NKR-CCR5). The dissociation constant of C-18 was calculated to be 3.646 nM compared with 0.559 nM for MIP-1β, suggesting a modest affinity. Importantly, the binding of C-18 to hCCR5-expressing cells was completely blocked by unlabeled C-18, but not by *P falciparum* cyclophilin, and was partially blocked by MIP-1β.[7] Here we demonstrate that the binding of radiolabeled C-18 to CEM.NKR-CCR5 cells is also partially blocked by soluble R5 gp120 (from Ba-L). Inhibition with X4 env (MN) was at least 10-fold less efficient and the small activity observed may be attributed to very low avidity binding to CCR5 due to common elements shared by CCR5 and CXCR4[30] (FIG. 3). Thus, it seems likely that the primary mechanism responsible for the inhibition of HIV-1 cell fusion mediated by *T gondii* C-18 is a steric inhibition of the interaction between gp120 and the CCR5 coreceptor, as has been previously demonstrated for several small molecule inhibitors.[10,31] This inhibitory mechanism differs from that of β-chemokine analogs, most of which act primarily by inducing receptor internalization (in addition to partial blocking of env-binding).

C-18 Blocks Fusion of Macrophages with R5 Envelope-expressing Cells

B-chemokines more effectively inhibit entry of HIV-1 into $CD4^+$ T cells than into macrophages or adherent cell lines cotransfected with huCD4 and coreceptor genes. While in some studies RANTES was observed to inhibit HIV infection of macrophages, prolonged presence of the inhibitor was required, suggesting the possible involvement of post-entry-inhibitory mechanisms.[32] This difference was correlated with the observation that β-chemokines and their derivatives induce CCR5 internalization and interfere with receptor recycling in T cells, but much less so in macrophages or adherent cells.[33-35] It was important, therefore, to determine if C-18 inhibits HIV fusion in macrophages with a similar efficiency as it does in T cells. Indeed, in 2 independent experiments, it was found that C-18 inhibited macrophage fusion with cells expressing R5 envelope with $ID_{50}$ values not significantly different from the $ID_{50}$ obtained with the T-cell line PM1 (Table 5). In the same experiments, inhibition by RANTES or MIP-β ranged between 20% and 30% at a concentration (100 ng/mL) previously shown to fully block HIV-1 infection in T cells (data not shown). Previously, we demonstrated that a combination of MIP-1aa, MIP-1β, and RAN-TES at this concentration incompletely blocked R5 fusion in macrophages, and this blocking was not dependent on G-protein signaling.[36] Thus, compared with β chemokines, C-18 fusion-blocking activity in macrophages is similar to its activity in T cells. These findings support the further development of C-18 as a broad inhibitor of R5 HIV-1 viruses that is likely to be active against infection of diverse types of primary target cells.

TABLE 2

*T. gondii* cyclophilin but not human or *P falciparum* cyclophilin Inhibits HIV-1 fusion

| Effector/target | Inhibitor (μg/mL)* | No. of syncytia | Inhibition, % |
|---|---|---|---|
| 12E1(JR-FLγPM) | None | 534 ± 50 | — |
| | c-18 (10) | 137 ± 74 | 74 |
| | Human cyclophilin (10) | 548 ± 51 | 0 |
| | *P falciparum* cyclophilin (10) | 552 ± 40 | 0 |

— indicates no inhibition.

*T. gondii* cyclophilin (C-18), human cyclophilin, or *P falciparum* cyclophilin was added to the PM1 target cells for one hour at 37° C. before addition of 12E1 cells expressing JR-FL envelope. Syncytia were scored after 3 hours. Representative of 3 experiments performed.

TABLE 3

STAg-derived cyclophilin (C-18) Inhibits Infectivity of HIV-1 R5 strains

| Virus | Clade | Coreceptor | Target cell | $ID_{50}$ μg/mL |
|---|---|---|---|---|
| JR-CSF | B (US) | CCR5 | PM1 | 0.4 |
| Ba-L | B (US) | CCR5 | PM1 | 3.8 |
| 92US657 | B (US) | CCR5 | PBMC | 2.1 |
| 92BE003 | B (Brazil) | CCR5 | PBMC | 2.7 |
| 92BR017 | B (Brazil) | CCR5 | PBMC | 4.0 |
| 92BR007 | C (Brazil) | CCR5 | PBMC | 14.0 |

TABLE 3-continued

STAg-derived cyclophilin (C-18) Inhibits Infectivity of HIV-1 R5 strains

| Virus | Clade | Coreceptor | Target cell | $ID_{50}$ µg/mL |
|---|---|---|---|---|
| 98CN009 | C (China) | CCR5 | PBMC | 3.3 |
| 98IN017 | C (India) | CXCR4 | PBMC | No Inhibitor |

PM1 cells were infected with the R5 virus (BA-L, JR-CSF) (100 $TCID_{50}$ per well). PBMCs were stimulated with PHA-P (0.25 µg/mL) and IL-2 (20 U/mL) for 3 days and were then infected with primary isolates (100 $TCID_{50}$ per well). C-18 protein (at serial 3-fold dilutions) was preincubated with the cells for one hour at 37° C. before addition of the virus (5 replicate per group). The virus was washed away after 2 days. Supernatants were collected every 2 days and assayed for p24 activity. The 50% viral inhibition does was calculated according to Reed and Muench as described by Shibata et al.[18] No inhibition with human cyclophilin.

TABLE 4

Inhibition of HIV-1 fusion by either STAg or C-18 is not mediated by production of the β-chemokines MIP-1α and MIP-1β.

| Inhibitor (does, µg/mL) | Antibodies (µg/mL) | No. of syncytia (1% inhibition) PM1/ 12E1(JR-FL Env) |
|---|---|---|
| None | None | 305 = 24 |
| STAg | — | 121 ± 10(60) |
|  | αMIP-1α/MIP-1β(2) | 124 ± 2(59) |
| C-18(10) | — | 72 ± 10(76) |
|  | αMIP-1α/MIP-1β(2) | 71 ± 12(77) |
| αMIP-1α/MIP-1β(2) | — | 53 ± 4(83) |
|  | αMIP-1α/MIP-1β(2) | 280 ± 32(8) |

— Indicates no antibody added.

MIP-1α and MIP-1β (Peprotech). STAg, or C-18 was added to PM1 cells alone or in the presence of a αMIP-1α/MIP-1β(2) antibodies for 60 minutes at 37° C. at the indicated concentrations. Then, 12E1 effector cells (infected overnight with vCB28) were added, and fusion was recorded after 3 to 4 hours.

TABLE 5

C-18 does not induce downmodulation of either CCR5 or CD4 on PM1 cells

| Treatment | ΔMFC† | |
|---|---|---|
|  | CCR5 | CD4 |
| None | 119 | 112 |
| RANTES + MIP-1β | 35 | 109 |
| C-18 | 104 | 105 |

*PM1 cells were incubated either with a mixture of RANTES and MIP-1β (1 µg/mL each) or with C-18 (10 µg/mL) for 2 hours at 37° C. The cells were then washed with staining buffer and were stained with FITC-conjugated 2D7 (anti-CCR5; Pharmingen) or FITC-conjugated Leu 3a (anti-hCD4; Becton Dickinson), or FITC-isotype control in the cold, and were analyzed by flow cytometry. Similar results were obtained after 18 hours of incubation of cells with C-18.
†Δ MFC values were calculated by subtracting the mean fluorescent channel (MFC) value of the isotype control from specific antibody staining.

Similar results were obtained with the cell lien CEM.N-RK.CCR5

TABLE 6

C-18 blocks fusions of cells expressing internalization-deficient CCR5 and of human macrophages

| | Fusion Inhibition with C-18, $ID_{50}$* | |
|---|---|---|
| Target cell | JR-FL Env, † µg/mL | Bal Env, † µg/mL |
| CEM WT CCR5.EGFP | 10.5 | 6.3 |
| CEM M7 CCR5.EGFP | 8.7 | 5.5 |
| PMI | 5.8 | 1.7 |
| Macrophages | 2.4 | 2.2 |

*C-18 (at 3-fold serial dilutions) was preincubated with target cells for one hour at 37° C. before mixing (at 1:1 ratio) with effector cells. Syncytia were scored at 3 hours for PM1 cells and at 20 hours for macrophages. The data are representative of 2 experiments performed.
†12E1 cells were infected overnight with either vCB28 (JR-FL Env) of vCB43 (Ba-L-Env) at 10 pfu/cell.

Molecular mimicry of chemokines ligands has been described for several pathogens and includes both structural homologs of known chemokines as well as structural mimicry without common sequences.[37] It was recently found that *T gondii* cyclophilin-18 constitutes a component of the IL-12-inducing activity of the parasite. C-18 was shown to activate murine dendritic cell via the chemokines receptor CCR5.

Unlike human CCR5, murine CCR5 is not functional as a HIV-1 coreceptor. However C-18 binds to CCR5 of both species, which share a high degree of homology. C-18 binds to human CCR5 with modest affinity compared with the biologic ligand MIP-1β. Nevertheless, this binding was sufficient to block HIV-1 env-medical cell fusion and infection of cell lines and PBMCs with cell-free virus including primary isolates.

The structural requirements for C-18-mediated CCR5 binding are under investigation. Other cyclophilins do not bind to CCR5 (ie, human cyclophilin and PfCyp19), implying that the peptidylprolyl isomerase enzymatic activity of C-18[9] is either not required or not sufficient for its CCR5-binding activity. However, cyclosporin A, an antagonist of cyclophilin, significantly reduced the HIV-1 inhibiting activity of C-18 (and also its IL-12-inducing activity in murine dendritic cells). This finding does not necessarily imply direct involvement of the cyclophilin active site in CCR5 binding. Rather it may reflect locking of C-18 in a conformational state less favorable for CCR5 binding.[21,22]

Previously described inhibitors that target HIV-1 coreceptors were shown to act by a plethora of mechanisms, inducing receptor internalization, interfering with receptor recycling, direct blocking of env-binding, or through some form of steric hindrance or conformational changes in the coreceptors.[10,25,33,38] C-18 did not induce CCR5 downmodulation, either in the absence or presence of anti-C-18 antibodies. This finding was surprising since C-18 signals through human CCR5, as determined by $ca^{++}$ mobilization and chemotaxis.[7] However, signaling is not always coupled with internalization. Internalization of GPCRs often requires phosphorylation. Internalization of GPCRs often requires phosphorylation of specific residues in the cycloplasmic tail and recruitment of intracellular adaptor molecules such as β-arrestin, which facilitates internalization.[39,40] Phorbol ester treatment induces rapid internalization of CXCR4 but not CCR5, even though both receptors undergo phosphorylation of the cycloplasmic tail.[41] The absence of a di-leucin motif in CCR5 may explain the inability of phorbol esters (or C-18) to induce CCR5 internalization.[42] Alternatively, C-18 may induce protein kinase C-mediated phosphorylation of CCR5, followed by a rapid dephosphyrrylation, previously described as a mechanism to maintain cell-membrane receptors in a nonphosphorylated, signaling-competent status.[43]

In our laboratory, chemokine-mediated inhibition of macrophage fusion with R5 viruses is inefficient, requiring high concentrations of β-chemokines, and does not involve receptor internalization.[10,33,36] In contrast, C-18 blocked HIV fusion of both T cells and macrophages with similar efficiencies. This finding further distinguishes C-18 from β-chemokines (or their derivatives) and places it in the class of inhibitors that do not require receptor downmodulation for efficient blocking of viral entry. A similar mechanism has been proposed for the small molecule R5 antagonist TAK 779,[27] the X4 antagonist AMD3100,[44,45] and small peptide-mimetops of RANTES.[38] Thus, C-18 represents a new type of microbial-derived product that may be developed as HIV-1 cell-entry inhibitor.

In the HIV-1 infectivity assays, the $ID_{50}$ values obtained with primary HIV-1 isolates from clades B and C ranged between 0.4 and 14 μg/mL.

The lack of CCR5 downmodulation will mean minimal perturbation to the normal function of CCR5-bearing cells. While C-18 binds to both murine and human CCR5, only the human chemokine receptor can support HIV-1 infection. This observation predicts that the critical contact residues on CCR5 for C-18 and HIV gp120 binding are not identical. However, some overlap must exist in order for C-18 to function as an inhibitor if HIV-1 cell entry. Indeed, R5 gp120 (Ba-L) partially inhibited the binding of iodinated C-18 to CCR5-expressing CEM cells, while X4 gp120 (MN) behaved as a much weaker competitor. Preliminary data suggest that C-18 also binds to rhesus CCR5 and blocks simian immunodeficiency virus infection.

REFERENCES

1. Berger E A, Murphy P M, Farber J M. Chemokine receptors as HIV-1 coreceptors: roles in viral entry, tropism, and disease. Annu Rev Immunol. 1999; 17:657-700.
2. Doranz B J, Baik S S, Doms R W. Use of a gp120 binding assay to dissect the requirements and kinetics of human immunodeficiency virus fusion events. J. Virol. 1999;73: 10346-10358.
3. Gosling J. Monteclaro F S, Atchison R E, et al. Molecular uncoupling of C—C chemokines receptor 5-induced chemotaxis and signal transduction form HIV-1 coreceptor activity. Proc Natl Acad Sci U.S.A. 1997;94:5061-5066.
4. Lee B, Sharron M, Blanpain C. et al. Epitope mapping of CCR5 reveals multiple conformational states and distinct but overlapping structures involved in chemokines and coreceptor function. J. Biol. Chem. 1999;274:9617-9626.
5. Wu L, Larosa G, Kassam N., et al. Interaction of chemokines receptor CCR5 with its ligands: multiple domains for chemokines binding. J Exp Med. 1997;186:1373-1381.
6. Alberti J, Reis e Sousa C, Schito M, et al CCR5 provides a signal for microbial induced production of IL-12 by CD8 alpha+ dendritic cells. Nat Immunol. 2000;1:83-87.
7. Alberti J, Valenzuela J G, Carruthers V B, et al. Molecular mimicry of a CCR5 binding-domain in the microbial activation of dendritic cells. Nat Immunol. 2003;4:485-490.
8. Grunvald E. Chiaramonte M, Hieny S, et al. Biochemical characterization and protein kinase C dependency of monokine-inducing activities of *Toxoplasma gondii*. Infect immune. 1996;64:2010-2018.
9. Berriman M, Fairlamb A H. Detailed characterization of a cyclophilin from the human malaria parasite *Plasmodium faciparum*. Biochem J. 1998;334(pt 2);437-445.
10. Brandt S M, Mariani R, Holland A U, Hope T J Landau N R. Association of chemokines-mediated block to HIV entry with coreceptor internalization. J Biol Chem. 2002; 227:17291-17299.
11. Lusso P, Cocchi F, Ballota C, et al. Growth of macrophase-tropic and primary human immuno-deficiency virus type 1 (HIV-1) isolates in a unique CD4+ T-cell clone (PM1): failure to down-regulate CD4 and to interfere with cell-line-tropic HIV-1. J. Virol. 1995;69;37112-3720
12. Trkola A. Matthews J, Gordon C, Ketas T, Moore J P. A cell line-based neutralization assay for primary human immunodeficiency virus type 1 isolates that use either the CCR5 or the CXCR4 co-receptor, J. Virol. 1999;73:8966-8974.13. Broder C C, Berger E A. Fusogenic selectivity of the envelope glycoprotein is a major determinant of human immunodeficiency virus type 1 tropism for CD4+ T-cell lines vs. primary macrophages. Proc Natl Acd Sci USA. 1995;92:9004-9008.
14. Hillman K, Shapira-Nahor O, Gruber M F, et al. Chemically induced CD4 mutants of a human T cell line; evidence for dissociation between binding of HIV-1 envelope and susceptibility to HIV-1 infection and syncytia formation. J. Immunol. 1990;144:2131-2139.
15. Jonak Z L, Clark R K, Matour D, et al. A human lymphoid recombinant cell line with functional human immunodeficiency virus type 1 envelope. AIDs Res Hum Retroviruses. 1993;9:23-32.
16. Shibata R, Siemon C, Czajak S C, Desrosiers R C, Martin M A, Live, attenuated simian immunodeficiency virus vaccines elicit potent resistance against a challenge with a human immunodeficiency virus type 1 chimeric virus. J Virol. 1997:71:8141-8148.
17. Zaitseva M, Blauvelt A, Lee S, et al. Expression and function of CCR5 and CXCR4 on human Langerhans cells and macrophages: Implications for HIV primary infection. Nat Med. 1997;3:1369-1375.
18. Lapharn C K, Zaitseva M B, Lee S. Romanstseva T, Golding H. Fusion of monocytes and macrophages with HIV-1 correlates with biochemical properties of CXCR4 and CCR5. Nat. Med. 1999;5:303-308.
19. Frankel S S, Steinman R M, Michael N L, et al. Neutralizing monoclonal antibodies block human immunodeficiency virus type 1 infection of dendritic cells and transmission to T cells. J Virol. 1998;72;9788-9794.20. Ferrantell F, Ruprecht R M. Neutralizing antibodies against HIV-back in the major leagues? Curr Opin Immunol. 2002;14:495-502.
21. Ivory M T. Immunophilins: switched on protein binding domains? Med Res Rev. 2000;20:452-484.
22. Hacker J. Fischer G. Immunophilins: structure-function relationship and possible role in microbial pathogenicity. Mol Microbiol. 1993:10:445-456.23. Wang J. Guan E, Rodriquez G, Norcross M A. inhibition of CCR5 expression by IL-12 through induction of beta-chemokines in human T lymphocytes. J. Immunol. 1999;163:5763-5769.
24. Brandt S M, Mariani R. Holland A U, Hope T J, Landau N R. Association of chemokines-mediated block to HIV entry with coreceptor internalization. J. Biol Chem. 2002; 277:17291-17299.
25. Signoret N, Peichen-Matthews A, Mack M Proudfoot A E, Marsh M. Endocytosis and recycling of the HIV coreceptor CCR5. J Cell Biol. 2000; 151:1281-1294.
26. Mack M. Luckow B, Nelson P J, et al. Aminooxypentane-RANTES induces CCR5 internalization but inhibits recycling: a novel inhibitory mechanism of HIV-1 infectivity. J. Exp Med. 1998;187:1215-1224.
27. Baba M, Nishimura O, Kanzaki N, et al. A small-molecule, nonpeptide CCR5 antagonist with highly potent and selective anti-HIV-1 activity. Proc Natl Acad Sci USA. 1999;96;5698-5703.
28. Dragic T, Trikola A, Thompson D A, et al. A binding pocket for a small molecule inhibitor of HIV-1 entry within the transmembranes helices of CCR5. Proc Natl Acad Sci USA. 2000;97:5639-5644.
29. Strizki J M, Xu S, Wagner N E, et al. SCH-C (SCH 351125), an orally bioavailable, small molecule antagonist of the chemokines receptor CCR5, is a potent inhibitor of HIV-1 infection in vitro and in vivo. Proc Natl Acad Sci USA. 2001;98:12718-12723.
30. Pontow S, Ratner L. Evidence for common structural determinants of human immunodeficiency virus type 1 coreceptor activity provided through functional analysis of CCR5/CXCR4 chimeric coreceptors. J. Virol 2001;75: 11503-11514.
31. Simmons G, Reeves J D, Hibbitts S, et al. Co-receptor use by HIV and inhibition of HIV infection by chemokines receptor ligands. Immunol. Rev. 2000;177:112-126.
32. Ylisastigui L, Vizzavona J, Drakopoulou E, et al. Synthetic full-length and truncated RANTES inhibit HIV-1 infection of primary macrophages. AIDS. 1998;12:977-984.
33. Simmons G. Clapham P R, Picard L, et al: Potent inhibition of HIV-1 infectivity in macrophages and lymphocytes by a novel CCR5 antagonist. Science 1997;276:276-279.
34. Dragic T, Litwin, Allaway G P, et al. HIV-1 entry into CD4+ cells is mediated by the chemokines receptor CC-CKR-5. Nature. 1996;381:667-673.
35. Schmidtmayerova H, Alfano M, Nuovo G, Bukrinsky M. Human immunodeficiency virus type 1 T-lymphotropic strains enter macrophages via a CD4- and CXCR4-mediated pathway: replication is restricted at a postentry level. J Virol. 1998;72:4633-4642.
36. Lee S, Lapham C K, Chen H, et al. Coreceptor competition for association with CD4 may change the susceptibility of human cells to infection with T-tropic and macrophagetropic isolates of human immunodeficiency virus type 1. J Virol. 2000;74:5016-5023.
37. Murphy P M. Viral exploitation and subversion of the immune system through chemokines mimicry. Nat Immunol. 2001;2:116-122.
38. Nardese V. Longhi R, Polo S, et al. Structural determinants of CCR5 recognition and HIV-1 blockade in RANTES. Nat. Struct Biol. 2001;8:611-615.
39. Kraft K, Olbrich H, Majoul I, Mack M, Proudfoot A, Oppermann M. Characterization of sequence determinants within the carboxyl-terminal domain of chemokines receptor CCR5 that regulate signaling and receptor internalization. J Biol Chem. 2001; 276:34408-34418.
40. Blanpain C, Wittamer V, Vanderwinden J M, et al. Palmitoylation of CCR5 is critical for receptor trafficking and efficient activation of intracellular signaling pathways. J. Biol Chem. 2001;276:23795-23804.
41. Golding H. Ouyang J. Zaitseva M; Broder C C, Dimitrov D S, Lapham C. increased association of glycoprotein 120-CD4 with HIV type 1 coreceptors in the presence of complex-enhanced anti-CD4 monoclonal antibodies. AIDS Res Hum Retroviruses. 1999;15:149-159.
42. Oppermann M, Mack M, Proudfoot A E, Olbrich H. Differential effects of CC chemokines on CC chemokine receptor 5 (CCR5) phosphorylation and identification of phosphorylation sites on the CCR5 carboxy terminus. J Biol. Chem. 1999;274: 8875-8885.
43. Pollok-Kopp B, Schwarze K, Baradari V K, Oppermann M. Analysis of ligand-stimulated CC chemokines receptor 5 (CCR5) phosphorylation in intact cells using phospho-site-specific antibodies. J Biol Chem. 2003;278:2190-2198.
44. Donzella G A, Schols D, Lin S W et al. AMD3100, a small molecule inhibitor of HIV-1 entry via the CXCR4 co-receptor. Nat. Med. 1998;4:72-77.
45. Schols D, Struyf S, Van Damme J, Este J A, Hanson G, De Clercq E. Inhibition of the chemokines receptor CXCR4. J Exp Med. 1997;186:1383-1388.

Incorporation by Reference

The contents of all references, patents, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting HIV infection of macrophages or T-cells comprising: contacting said macrophage or T-cell with an effective amount of a cyclophilin, or biologically active fragment thereof, wherein the cyclophilin or fragment thereof is capable of inhibiting HIV infection of a cell; thereby inhibiting the infection of macrophages or T-cells by HIV.

2. The method of claim 1, wherein the HIV is a CCR5 specific HIV.

3. The method of claim 1, wherein the cyclophilin, or biologically active fragment thereof, is encoded by a nucleic acid molecule that is at least 85% identical to SEQ ID NO:1, or a fragment thereof.

4. The method of claim 1, wherein the cyclophilin, or biologically active fragment thereof, is encoded by a nucleic acid molecule that is at least 95% identical to SEQ ID NO:1, or a fragment thereof.

5. The method of claim 1, wherein the cyclophilin, or biologically active fragment thereof, is encoded by a nucleic acid molecule of SEQ ID NO:1, or a fragment thereof.

6. The method of claim 1, wherein the cyclophilin, or biologically active fragment thereof, has an amino acid sequence that is at least 85% identical to SEQ ID NO:2, or a fragment thereof.

7. The method of claim 1, wherein the cyclophilin, or biologically active fragment thereof, has an amino acid sequence that is at least 95% identical to SEQ ID NO:2, or a fragment thereof.

8. The method of claim 1, wherein the cyclophilin, or biologically active fragment thereof, has the amino acid sequence of SEQ ID NO:2, or a fragment thereof.

9. The method of claim 1, wherein the cyclophilin is a protozoan cyclophilin.

10. The method of claim 9, wherein the cyclophilin is from the genus *Toxoplasma*.

11. The method of claim 10, wherein the cyclophilin is from the species *gondii*.

* * * * *

SEQUENCE LISTING

```
<160> NUMBER OF SEQ ID NOS: 2

<210> SEQ ID NO 1
<211> LENGTH: 697
<212> TYPE: DNA
<213> ORGANISM: Toxoplasma gondii

<400> SEQUENCE: 1
aattccaaaa tgaagctcgt gctgttttc ctcgctcttg cggtgtctgg cgccgtggca      60
gaaaatgccg gagtcagaaa ggcgtacatg gatatcgaca tcgacggaga acatgccggg     120
cgcattatct tggagctccg tgaggacatc gctcccaaaa ctgtcaagaa cttcattggc     180
cttttcgaca agtacaaggg cagcgttttc caccgtatca tccccgactt catgatccag     240
```

-continued

```
ggaggagatt tcgagaacca caacggcact ggaggacaca gcatctacgg ccgaagattt    300
gacgacgaaa actttgattt gaagcacgag cgaggcgtca tctctatggc gaacgccggt    360
ccgaacacca atggcagcca atttttcatc accaccgtga agacagagtg gctcgacgcc    420
agacacgttg ttttcgggaa gatcacaact gagtcgtggc ctaccgtcca ggctattgag    480
gctctcggcg gcagcggcgg ccgcccgtct aaggtcgcga aaatcacgga cattggtttg    540
ttggagtaaa tcgagaagat cctgtgtaca tctggatgca cgtgtcgttt ccctgatat     600 ctattcgtgt gagcaagtgt gccctcttcc cgacgaaagt ggggagtcca caccactgaa    660
cgttttttta aacatttcta aatactagac tctgtcg                             697
```

<210> SEQ ID NO 2
<211> LENGTH: 179
<212> TYPE: PRT
<213> ORGANISM: Toxoplasma gondii

<400> SEQUENCE: 2

```
Met Lys Leu Val Leu Phe Phe Leu Ala Leu Ala Val Ser Gly Ala Val
  1               5                  10                  15

Ala Glu Asn Ala Gly Val Arg Lys Ala Tyr Met Asp Ile Asp Ile Asp
             20                  25                  30

Gly Glu His Ala Gly Arg Ile Ile Leu Glu Leu Arg Glu Asp Ile Ala
         35                  40                  45

Pro Lys Thr Val Lys Asn Phe Ile Gly Leu Phe Asp Lys Tyr Lys Gly
     50                  55                  60

Ser Val Phe His Arg Ile Ile Pro Asp Phe Met Ile Gln Gly Gly Asp
 65                  70                  75                  80

Phe Glu Asn His Asn Gly Thr Gly Gly His Ser Ile Tyr Gly Arg Arg
                 85                  90                  95

Phe Asp Asp Glu Asn Phe Asp Leu Lys His Glu Arg Gly Val Ile Ser
            100                 105                 110

Met Ala Asn Ala Gly Pro Asn Thr Asn Gly Ser Gln Phe Phe Ile Thr
        115                 120                 125

Thr Val Lys Thr Glu Trp Leu Asp Ala Arg His Val Val Phe Gly Lys
    130                 135                 140

Ile Thr Thr Glu Ser Trp Pro Thr Val Gln Ala Ile Glu Ala Leu Gly
145                 150                 155                 160

Gly Ser Gly Gly Arg Pro Ser Lys Val Ala Lys Ile Thr Asp Ile Gly
                165                 170                 175

Leu Leu Glu
```